(12) United States Patent
Cao et al.

(10) Patent No.: US 12,275,925 B2
(45) Date of Patent: Apr. 15, 2025

(54) BIOREACTOR AND RESEEDING CHAMBER SYSTEM AND RELATED METHODS THEREOF

(71) Applicants: UNIVERSITY OF VIRGINIA PATENT FOUNDATION, Charlottesville, VA (US); Yiqi Cao, Blacksburg, VA (US); Lydia Luu, Fairfax, VA (US); Wade Zhang, Charlottesville, VA (US); George Christ, Charlottesville, VA (US); Kimberly C. Smith, Charlottesville, VA (US)

(72) Inventors: Yiqi Cao, Blacksburg, VA (US); Lydia Luu, Fairfax, VA (US); Wade Zhang, Charlottesville, VA (US); George Christ, Charlottesville, VA (US); Kimberly C. Smith, Charlottesville, VA (US)

(73) Assignee: University of Virginia, Charlottesville, VA (US)

( * ) Notice: Subject to any disclaimer, the term of this patent is extended or adjusted under 35 U.S.C. 154(b) by 897 days.

(21) Appl. No.: 15/760,009

(22) PCT Filed: Sep. 15, 2016

(86) PCT No.: PCT/US2016/051948
§ 371 (c)(1),
(2) Date: Mar. 14, 2018

(87) PCT Pub. No.: WO2017/048961
PCT Pub. Date: Mar. 23, 2017

(65) Prior Publication Data
US 2018/0265831 A1    Sep. 20, 2018

Related U.S. Application Data

(60) Provisional application No. 62/218,712, filed on Sep. 15, 2015.

(51) Int. Cl.
*C12M 3/00*      (2006.01)
*C12M 1/12*      (2006.01)
*C12M 1/42*      (2006.01)

(52) U.S. Cl.
CPC .......... *C12M 21/08* (2013.01); *C12M 25/14* (2013.01); *C12M 35/00* (2013.01); *C12M 35/04* (2013.01); *C12N 2513/00* (2013.01)

(58) Field of Classification Search
USPC ...................................................... 435/289.1
See application file for complete search history.

(56) References Cited

U.S. PATENT DOCUMENTS

| | | | |
|---|---|---|---|
| 10,071,185 B2 * | 9/2018 | Cohen | C12M 23/26 |
| 2001/0003653 A1 * | 6/2001 | Banes | C12M 35/04 |
| | | | 435/293.1 |

(Continued)

FOREIGN PATENT DOCUMENTS

| | | |
|---|---|---|
| CN | 102433258 A | 5/2012 |
| EP | 1 734 110 A1 | 12/2006 |
| WO | 2012/021814 A2 | 2/2012 |

OTHER PUBLICATIONS

"NUNC™ 1-, 4- and 8-Well Rectangular Dishes". Laboratory Network. Aug. 1, 2005. (Year: 2005).*

(Continued)

*Primary Examiner* — Holly Kipouros
*Assistant Examiner* — Nathan G Esperon
(74) *Attorney, Agent, or Firm* — WHDA, LLP

(57) ABSTRACT

An integrated bioreactor and reseeding chamber system and a separate bioreactor and complimentary reseeding chamber system comprising a bioreactor and a separate reseeding chamber. The bioreactor comprises a bioreactor chamber; a first groove attached to the bioreactor chamber; a second groove removably attached to the bioreactor chamber. A first bar and a second bar may be removably inserted into the first (Continued)

groove and the second groove respectively. Each of the first bar and the second bar may have at least an oval hole. At least a crossbar is attached substantially perpendicularly to the first bar and the second bar to form a crossbar-bars construct through the oval holes. A knob may be installed on each of the crossbars. The reseeding chamber may comprise dividers fixedly attached to a bottom of the reseeding chamber.

36 Claims, 13 Drawing Sheets

(56) References Cited

U.S. PATENT DOCUMENTS

| | | | |
|---|---|---|---|
| 2004/0219659 A1 | 11/2004 | Altman et al. | |
| 2006/0141623 A1 | 6/2006 | Smith et al. | |
| 2006/0239981 A1* | 10/2006 | Yoo | A61L 27/3604 435/325 |
| 2010/0144007 A1* | 6/2010 | Bryant | F16H 21/44 100/280 |
| 2010/0197020 A1* | 8/2010 | Cao | A61L 27/58 435/395 |
| 2010/0323438 A1 | 12/2010 | Porter et al. | |
| 2011/0008397 A1* | 1/2011 | Cohen | A61K 35/12 435/395 |
| 2011/0172683 A1 | 7/2011 | Yoo et al. | |
| 2011/0212500 A1 | 9/2011 | Boronyak et al. | |
| 2012/0100602 A1* | 4/2012 | Lu | C12M 35/04 435/289.1 |
| 2013/0197640 A1* | 8/2013 | Christ | A61F 2/08 435/395 |

OTHER PUBLICATIONS

Weiss, S., Henle, P., Roth, W., Bock, R., Boeuf, S. and Richter, W. (2011), Design and characterization of a new bioreactor for continuous ultra-slow uniaxial distraction of a three-dimensional scaffold-free stem cell culture. Biotechnol Progress, 27: 86-94. https://doi.org/10.1002/btpr.510 (Year: 2011).*

Beca, Bogdan. "A Platform for High-throughput Mechanobiological Stimulation of Engineered Microtissues". 2012. https://tspace.library.utoronto.ca/bitstream/1807/32525/1/Beca_Bogdan_201206_MASc_thesis.pdf (Year: 2012).*

Thermo Scientific. "Thermo Scientific Microplates Guide". 2014. https://www.kisker-biotech.com/frontoffice/fiches_techniques/display?refId=056276&originalFileName=056276_BRen.pdf&newFileName=Technical_sheets_-_Rectangular_dishes_1%2C_2%2C_4_chambers_-_056276_-_Brochure.pdf (Year: 2014).*

Kurpinski K., Li S., "Mechanical Stimulation of Stem Cells Using Cyclic Uniaxial Strain", J. Visualized Exp. 6. http://www.jove.com/index/Details.stp?ID=242, doi: 10.3791/242. See video at: https://www.ncbi.nlm.nih.gov/pmc/articles/PMC2557108/ (Year: 2007).*

Machingal, Masood A., et al., "A Tissue-Engineered Muscle Repair Construct for Functional Restoration of an Irrecoverable Muscle Injury in a Murine Model", Tissue Engineering: Part A, Sep. 1, 2011, vol. 17, No. 17-18, pp. 2291-2303.

Extended Search Report dated Apr. 30, 2019, issued in counterpart EP Application No. 16847304.9 (26 pages).

PCT ISR and Written Opinion, PCT/US16/51948, Dec. 30, 2016.

International Preliminary Report on Patentability (Form PCT/IB/326) issued in counterpart International Application No. PCT/US2016/051948 dated Mar. 29, 2018, with Forms PCT/IB/373 and PCT/ISA/237 (5 pages).

International Search Report dated Dec. 30, 2016, issued in counterpart International Application No. PCT/US16/51948 (5 pages).

* cited by examiner

A.

B.

BIOREACTOR AND RESEEDING CHAMBER SYSTEM AND RELATED METHODS THEREOF

CROSS-REFERENCE TO RELATED APPLICATIONS

This application claims the benefit of the filing date of U.S. Provisional Patent Application No. 62/218,712 filed on Sep. 15, 2015, the disclosure of which is hereby incorporated by reference.

FIELD OF THE INVENTION

This invention relates to a bioreactor and reseeding chamber system and, more particularly, to a bioreactor and related methods thereof.

BACKGROUND OF THE INVENTION

Volumetric muscle loss (VML) is the traumatic or surgical loss of skeletal muscle that results in irrecoverable functional impairment, ranging from disfigurement to life-long disability. Patients with VML cannot recover because their bodies cannot regenerate the lost muscle. Annually, at least 20 million automobile accidents result in traumatic injury to the extremities. In addition, 70% of battlefield injuries are musculoskeletal in nature. Congenital VML also plays a role. Each year, 4,440 babies are born with cleft lip with or without cleft palate and 2,650 babies are born with cleft palate.

Current treatment options include functional free muscle transfer to the injury site and physical therapy. The results of free muscle transfer are inconsistent and depend on the skill of the surgeon. Physical therapy has not been shown to significantly improve recovery after VML and does not restore skeletal muscle fibers. There are tissue engineering approaches currently under development to treat VML. However, there is significant room for therapeutic improvement in the timeliness and magnitude of recovery.

Corona et al. [Corona, B. T., Ward, C. L., Baker, H. B., Walters, T. J. & Christ, G. J. *Tissue Eng. Part A* 20, 705-715 (2013)] demonstrated that a tissue engineered muscle repair (TEMR) construct improves functional recovery capabilities of lost musculature. The construct involves muscle-derived cells seeded onto a bladder acellularized scaffold (BAM), which is then preconditioned in a bioreactor under cyclical mechanical loading to produce a myogenic cellular phenotype for implantation into a VML rat model. This construct restored function by approximately 70%. However, different cellular phenotypes in the construct, from organization of muscle derived cells to the density and composition of myoblasts and multinucleated myotubes, yield varying results on functional recovery in vivo. Further development of the TEMR construct requires an improved understanding of the mechanical and biological mechanisms in vitro that affect the speed and magnitude of functional recovery of skeletal musculature following implantation in vivo, for the long-term goal of developing a tissue engineered construct for effective, reproducible, and prolonged muscle repair.

Cyclic mechanical strain affects proliferation, gene expression, and synthesis of matrix proteins, and other cellular activities of tissues. There are many existing bioreactor designs that apply cyclic mechanical stretch for various tissues, including muscle, tendon, cartilage, bone, and many tissue composites. While Corona et al. showed that multiple cell seeding steps can produce more differentiated myogenic phenotypes, there currently does not exist any commercially available or published systems to allow for consistent cell reseeding on the scaffold.

Giannitsios et al. (T Jim, B; Giannitsios, D; Beckman, L; Steffen, 'Novel Dynamic Axial Loading Bioreactor: Design And Validation With Bovine Intervertebral Discs', 5th Combined Meeting of the Orthopaedic Research Societies of Canada, USA, Japan and Europe, 2003) report a bioreactor, as shown in FIG. 1A. Saber et al. (Sepideh Saber and others, 'Flexor Tendon Tissue Engineering: Bioreactor Cyclic Strain Increases Construct Strength', Tissue Engineering—Part A, 16.6 (2010), 2085-90) report another custom bioreactor design, as shown in FIG. 1B. However, these designs are not high throughput, and the vertical designs do not allow reseeding of the cell scaffold. Wunderli et al. (Stefania L. Wunderli and others, 'Minimal Mechanical Load and Tissue Culture Conditions Preserve Native Cell Phenotype and Morphology in Tendon—a Novel Ex Vivo Mouse Explant Model', Journal of Orthopaedic Research, 36.5 (2018), 1383-90) allegedly report a high-throughput bioreactor for loading tendon explants (FIG. 1C), but this design also does not allow for reseeding the cells on both sides of the scaffolds, which are secured vertically in the bioreactor. There are also BOSE ELECTROFORCE® multi-specimen BIODYNAMIC® test instruments (FIG. 1D). However, these instruments are simply machines for testing, and are not designed to support cell growth. Bose also produces the ELECTROFORCE® planar biaxial TestBench instrument (FIG. 1E). However, this testing machine is also not designed to support cell growth. The FLEXCELL® FX-5000™ Tension System is a bioreactor (FIG. 1F). However, such bioreactor requires cells be seeded onto a culture plate on the bottom of the bioreactor. Thus, it does not allow for the use of a biological scaffold such as the BAM, which is necessary for implantation into an animal model. Multiple cell seeding steps have been shown to produce more differentiated myogenic phenotypes and thus potentially improve functional capacity, but no currently available bioreactor design allows for the consistent reseeding of cells on both sides of the scaffold.

BRIEF SUMMARY

Accordingly, one example of the present invention is a bioreactor. The bioreactor comprises a bioreactor chamber; a first groove attached to the bioreactor chamber; a second groove removably attached to the bioreactor chamber. A first bar and a second bar (referred as gray bars in the provisional application) may be removably inserted into the first groove and the second groove respectively. Each of the first bar and the second bar may have at least an oval hole. The second groove is movable and capable of sliding back and forth along a direction perpendicular to the first groove. The bioreactor may further comprise at least a crossbar attached substantially perpendicularly to the first bar and the second bar to form a crossbar-bars construct through the oval holes. The first bar and the second bar may be kept at fixed positions by the crossbar. A knob may be installed on each of the crossbars. The crossbar-bars construct may be readily removed from as well as inserted back into the bioreactor chamber.

Accordingly, another example of the present invention is a separate bioreactor and complementary reseeding chamber system comprising a bioreactor and a separate reseeding chamber. The reseeding chamber is so dimensioned to be capable of housing a crossbar-bars construct removed from the bioreactor. The reseeding chamber may comprise dividers fixedly attached to a bottom of the reseeding chamber. The dividers may form separate compartments inside the reseeding chamber. The dividers may be plastic dividers.

Accordingly, another example of the present invention is an integrated bioreactor and reseeding chamber system wherein the bioreactor chamber is the same as the reseeding chamber. The bioreactor chamber may comprise dividers fixedly attached to a bottom of the bioreactor chamber. The dividers may form separate compartments inside the bioreactor chamber. The dividers may be plastic dividers.

The present novel bioreactor may precondition TEMR constructs under cyclical, mechanical stretch, while allowing for multiple iterations of cell seeding on the scaffold, with potentially multiple cell types (e.g., satellite cells, myoblasts, fibroblasts, endothelial cells, other stem or progenitor cells). To avoid perturbing the system, an aspect of an embodiment of the present invention bioreactor features a removable construct that secures the scaffold in place, and can be reinserted into a separate reseeding chamber or the same bioreactor chamber to seed the underside of the scaffold. The present inventors also built a new graphic user interface (GUI) that reduces the number of steps and time spent to program a cyclic stretch protocol for the bioreactor by 38% and 45%, respectively. An aspect of an embodiment of the present invention bioreactor system shall improve functional outcomes in muscle regeneration to treat VML injuries.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

DETAILED DESCRIPTION

Figure 1:
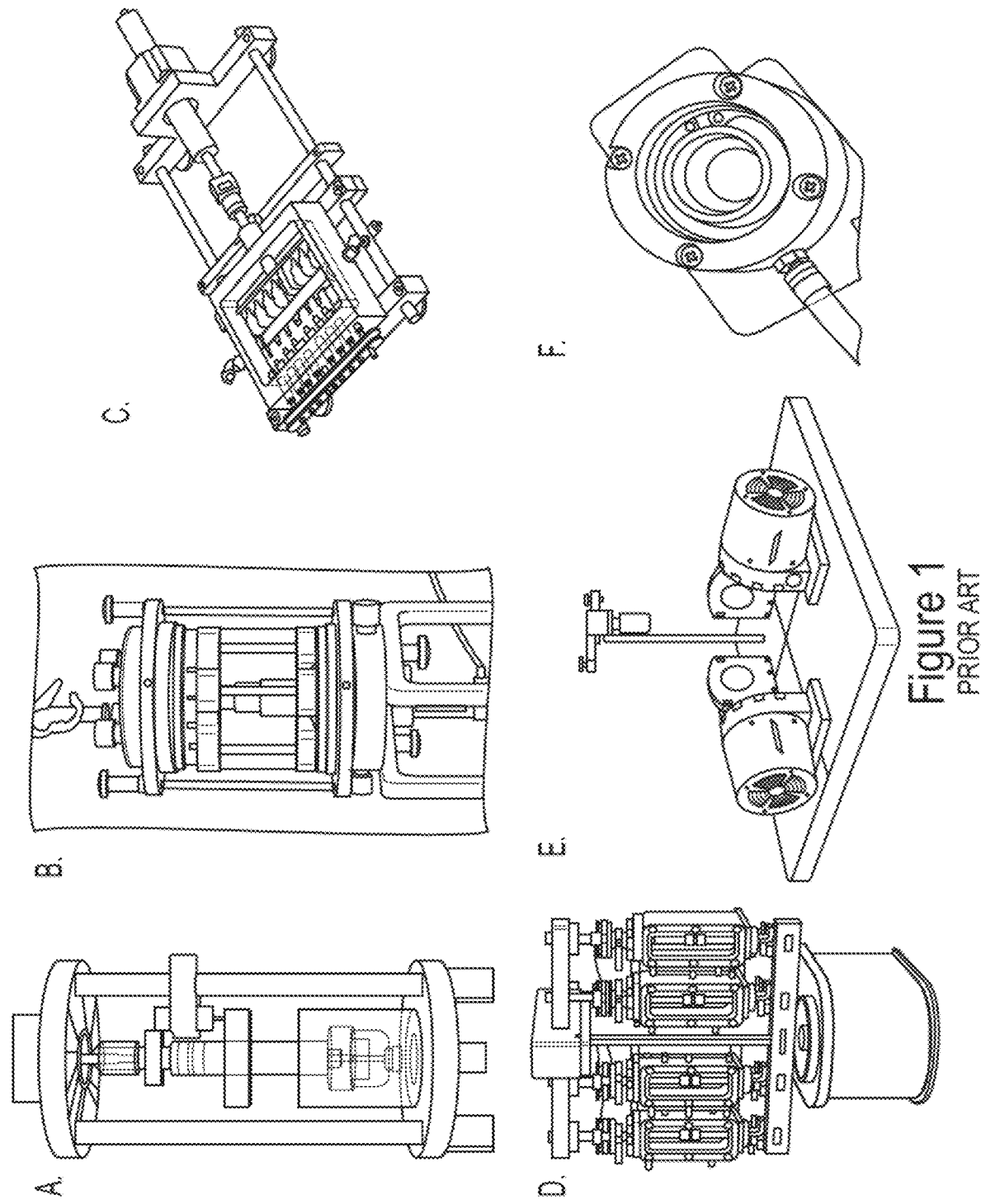
FIG. 1 shows published or commercially available cyclic loading bioreactors. A) A controlled bioreactor environment for incubating bovine intervertebral disks under dynamic axial loading. B) A custom cylindrical, vertical loading chamber for applying uniaxial tension to tendon constructs. C) A scalable, high-throughput bioreactor for cyclically loading tendon explants D) Bose ElectroForce® multi-specimen BioDynamic® test instrument. E) Bose ElectroForce® planar biaxial TestBench instrument. F) Flexcell® FX-5000™ Tension System.

The present invention is described with reference to embodiments of the invention. Throughout the description of the invention, reference is made to FIGS. 1-11. When referring to the figures, like structures and elements shown throughout are indicated with like reference numerals.

Figure 2:
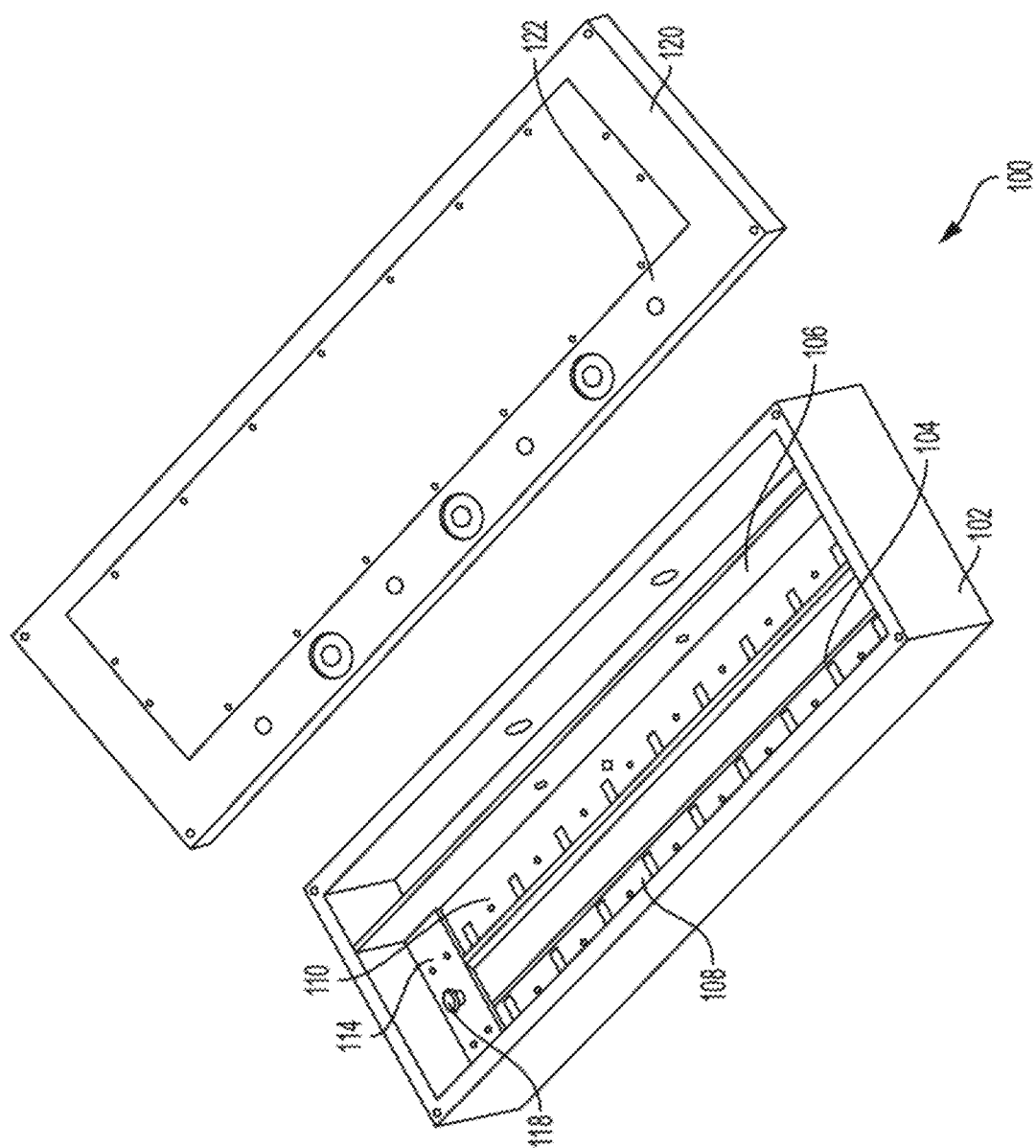
FIG. 2 shows a CAD drawing of a bioreactor and a lid.

FIG. 2 shows a CAD drawing of a bioreactor in accordance with one embodiment of the present invention. According to this embodiment, the bioreactor 100 comprises a bioreactor chamber 102; a first groove 104 attached to the bioreactor chamber 102; a second groove 106 removably attached to the bioreactor chamber 102. A first bar 108 and a second bar 110 may be removably inserted into the first groove 104 and the second groove 106 respectively. The first bar 108 and the second bar 110 may be inserted into and removed out of the first groove 104 and the second groove 106 respectively. The second groove 106 is movable and capable of sliding back and forth along a direction perpendicular to the first groove 104. The second groove 106 may be connected to a stepper motor, which is capable of applying a cyclic loading onto the second groove 106. The first groove 104 may be substantially parallel to the second groove 106. The bioreactor chamber 102 may be in a shape of a rectangular box.

In one embodiment, the bioreactor may further comprise at least a crossbar 114 attached to the first bar 108 and the second bar 110 to form a crossbar-bars construct 116. The first bar 108 and the second bar 110 may be kept at fixed positions by the crossbar 114 to form a fixed crossbar-bars construct 116. The fixed crossbar-bars construct 116 may be readily removed from the bioreactor chamber 102. The crossbar 114 may be attached substantially perpendicularly to the first bar 108 and the second bar 110 to form the crossbar-bars construct 116. In one embodiment, the crossbar 114 may be attached substantially perpendicularly to a position near an end of the first bar 108 and a position near an end of the second bar 110. The means for attaching the crossbar 114 to the first bar 108 and the second bar 110 is not limited. In one embodiment, the means for attaching the crossbar 114 to the first bar 108 and the second bar 110 is by screws 115. The crossbar-bars construct 116 may be readily lifted out of the bioreactor chamber 102 as well as inserted back into the bioreactor chamber 102. A knob 118 may be installed on the crossbar 114.

Figure 3:
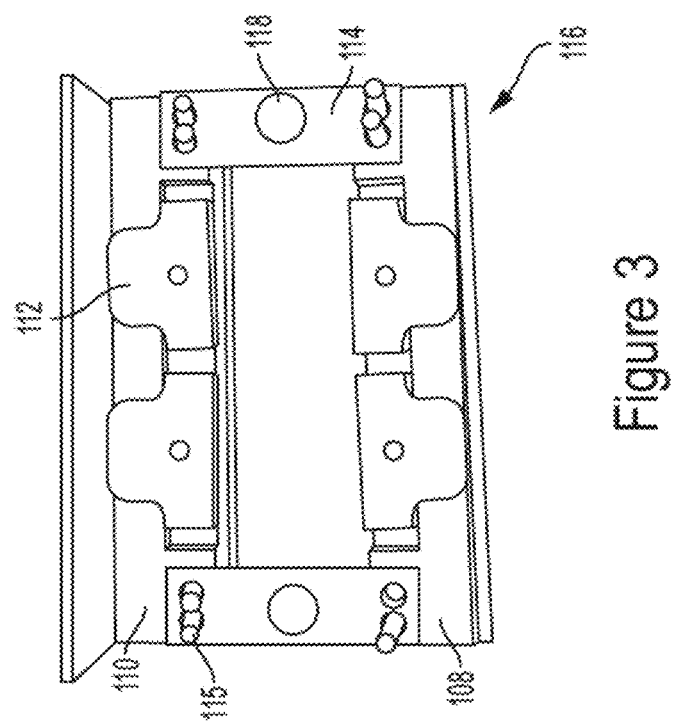
FIG. 3 shows a crossbar-bars construct.

FIG. 3 shows a crossbar-bars construct removed from the bioreactor chamber. In one embodiment, the bioreactor 100 further comprises two crossbars 114, each of the two crossbars 114 attached substantially perpendicularly to both the first bar 108 and the second bar 110 to form a fixed crossbar-bars construct 116. The first bar 108 and the second bar 110 are kept at fixed positions by the two crossbars 114 to form a fixed crossbar-bars construct 116. In one embodiment, each of the two crossbars 114 is attached substantially perpendicularly to a position near an end of the first bar 108 and a position near an end of the second bar 110. The crossbar-bars construct 116 may be readily lifted out of the bioreactor chamber 102 as well as inserted back into the bioreactor chamber 102. A knob 118 may be installed on each of the two crossbars 114.

In one embodiment of this invention, a means for securing a scaffold may be installed on the first bar and the second bar respectively to form a pair facing each other. The means for securing a scaffold is not limited. In one embodiment, the means for securing a scaffold may be a tab 112, clip, clamp, or a hooker.

In another embodiment of this invention, a number of means for securing a scaffold may be installed on the first bar and the second bar respectively to form a number of pairs. Each of the means for securing a scaffold on the first bar may face another means for securing a scaffold on the second bar. The number of the pair of the means for securing a scaffold on the first bar and on the second bar is not limited. Preferably, there may be two to eight pairs of means for securing a scaffold on the first bar and the second bar. In one embodiment, the means for securing a scaffold may be a tab 112, clip, clamp, or a hooker.

Figure 4:
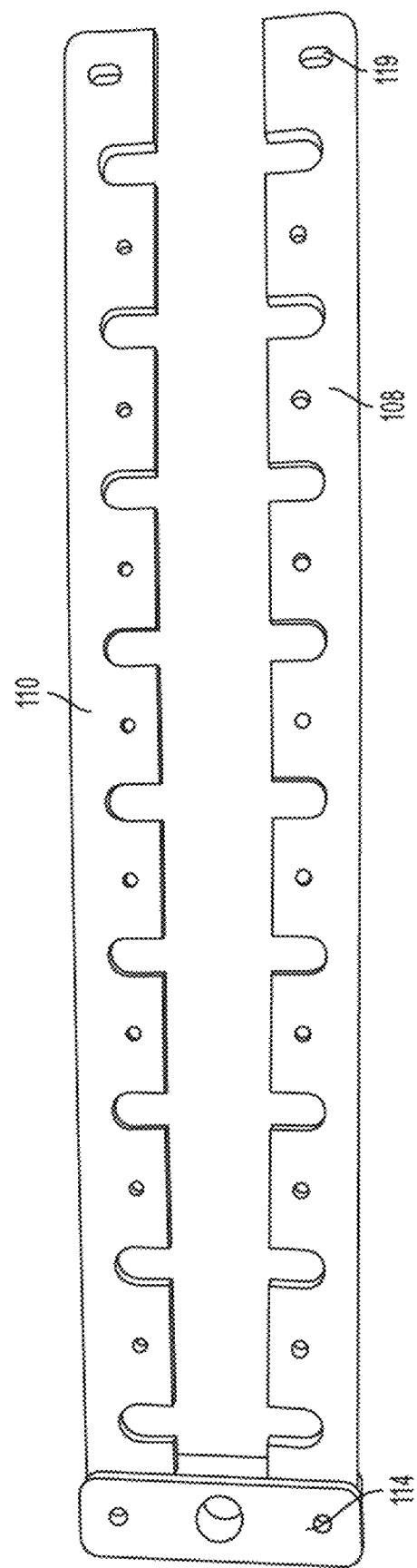
FIG. 4 shows another embodiment of a partial crossbar-bars construct.

FIG. 4 shows another embodiment of a partial crossbar-bars construct. In one embodiment, each of the first bar and the second bar has at least one oval hole 119. In another embodiment, each of the first bar and the second bar may have two oval holes 119. These oval holes 119 may be positioned near both ends of the first bar and the second bar respectively. The crossbars may be attached to the first bar and the second bar through screws passing these oval holes 119. This crossbar-bars construct with oval holes would allow for lateral displacement of the bars, even though one of them is in a fixed position.

In one embodiment, the bioreactor 100 may further comprise a lid 120 for the bioreactor chamber 102. The lid 120 may contain holes 122 for air filters, to prevent biocontamination with the air and condensation.

In one embodiment, the bars are used to secure scaffolds across the bioreactor. The bars are removably inserted into the grooves. The crossbars are fixed to the bars before removing the bar/scaffold construct for reseeding.

Figure 5:
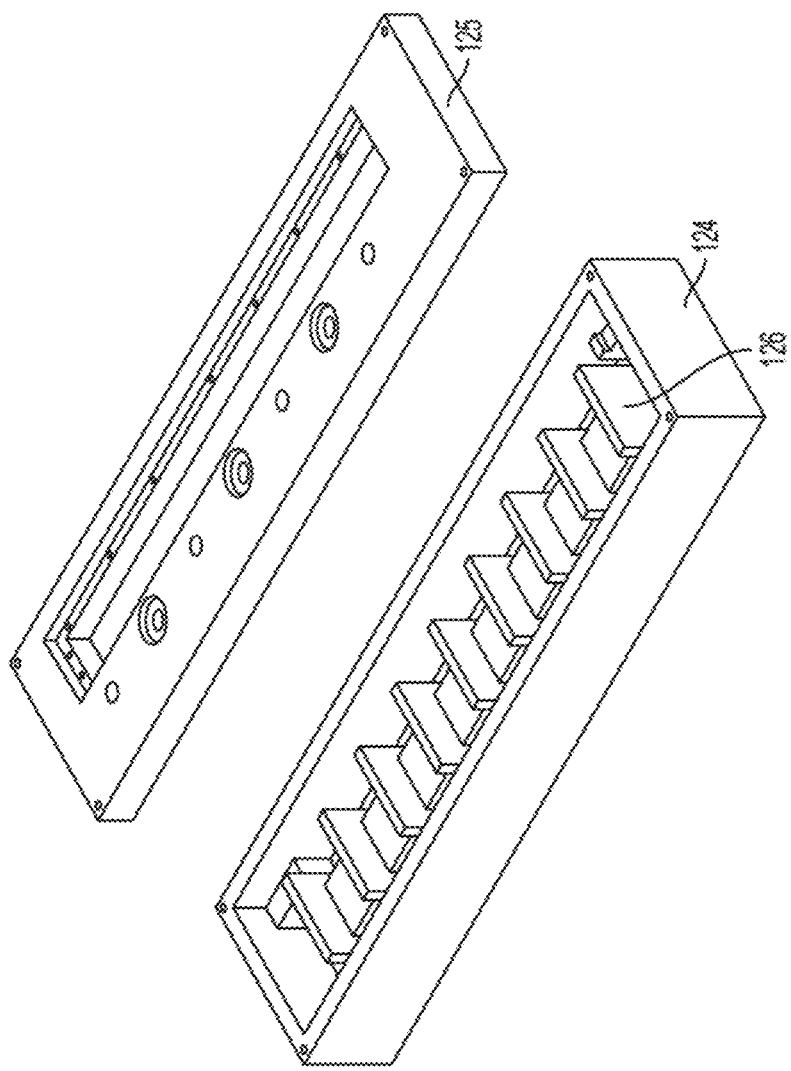
FIG. 5 shows a CAD drawing of a reseeding chamber with a lid.

FIG. 5 shows a CAD drawing of a reseeding chamber 124 with a lid 125 in accordance with one embodiment of the present invention. In one embodiment, the reseeding chamber 124 may be used together with a bioreactor 100 to form a separate bioreactor and complementary reseeding chamber system. The reseeding chamber 124 is so dimensioned to be capable of housing a crossbar-bars construct 116 removed from the bioreactor 100. In one embodiment, the reseeding chamber 124 may comprise dividers 126 attached to a bottom of the reseeding chamber 124. In one embodiment, the dividers 126 may be fixedly attached to the bottom of the reseeding chamber 124. The dividers 126 may be fixedly attached to the bottom of the reseeding chamber 124 at even intervals.

Figure 6:
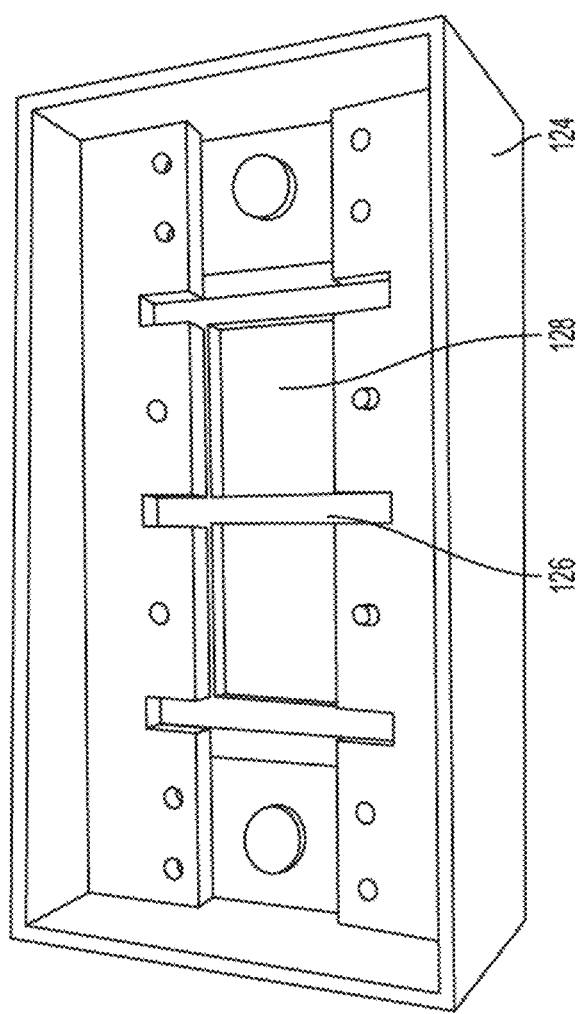
FIG. 6 shows a reseeding chamber housing a crossbar-bars construct.

FIG. 6 shows a reseeding chamber inserted with a crossbar-bars construct 116. The dividers 126 may form separate compartments 128 inside the reseeding chamber 124. The dividers 126 may be plastic dividers. The number of the dividers 126 in the reseeding chamber 124 is not limited. Preferably, there are at least three dividers 126 inside the reseeding chamber.

Figure 7B:
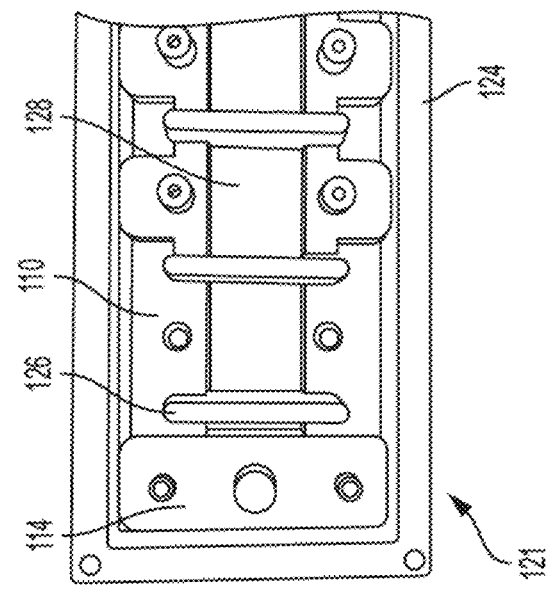
FIG. 7 shows the removable components (bars and cross bars) in a reseeding chamber system (A) full view; (B) partial view.
Figure 7A:
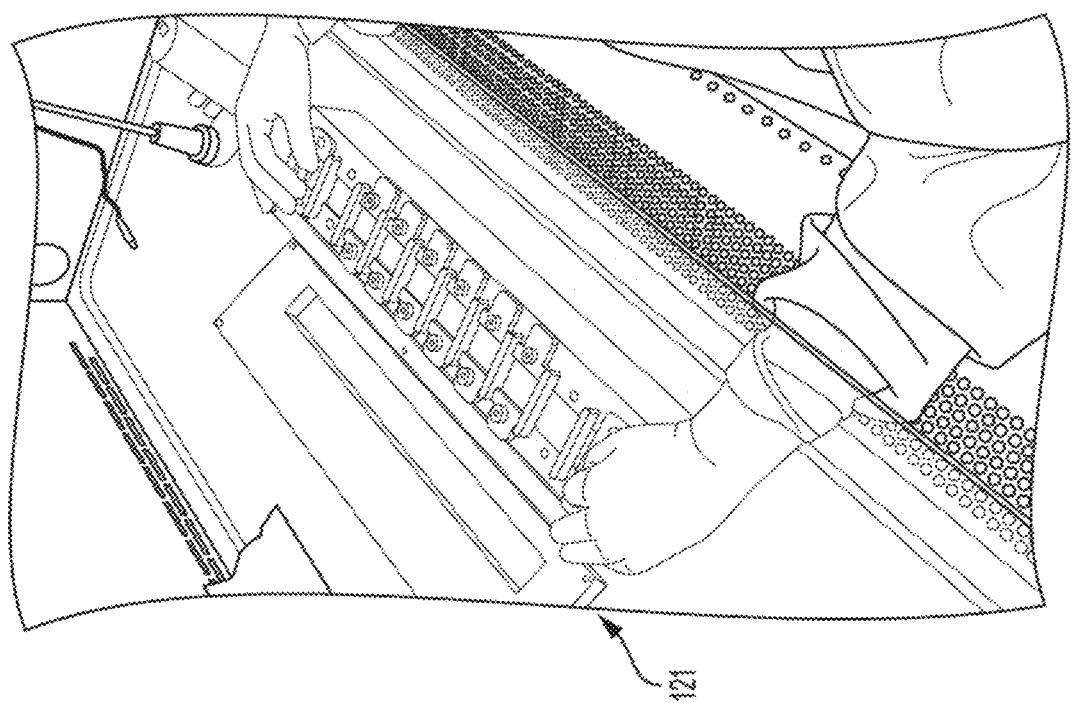

FIG. 7 shows a full view and a partial view of a reseeding chamber system 121 in accordance with one embodiment of the present invention. In one embodiment, the reseeding chamber is also used as a bioreactor chamber to form an integrated bioreactor and reseeding chamber system. The reseeding chamber 124 may comprise dividers 126 attached to a bottom of the reseeding chamber 124. In one embodiment, the dividers 126 may be fixedly attached to the bottom of the reseeding chamber 124. The dividers 126 may be fixedly attached to the bottom of the reseeding chamber 124 at even intervals. The dividers 126 may form separate compartments 128 inside the reseeding chamber 124. The dividers 126 may be plastic dividers. The integrated bioreactor and reseeding chamber system 121 would allow reseeding of cells on a scaffold in the same bioreactor chamber, thereby eliminating the process of moving the scaffold from a bioreactor chamber to another separate reseeding chamber.

In one embodiment, the bioreactor may be used in a method of seeding cells onto a scaffold. In another embodiment, the separate bioreactor and reseeding chamber system may be used in a method of seeding cells onto a scaffold. The method of seeding cells onto a scaffold may comprise securing a scaffold having a bottom side and a top side onto the first bar and the second bar of the bioreactor. The bars secure the scaffold across the bioreactor. Then, the second groove may be slid cyclically to apply a cyclic load onto the scaffold. Crossbars may be fixed to the bars before removing the crossbar-bars construct with the scaffold for reseeding. Then, the crossbar-bars construct with the scaffold may be lifted out of the bioreactor and inserted into the reseeding chamber. The top side of the scaffold may be seeded. Then, the crossbar-bars construct with the scaffold may be turned upside down inside the reseeding chamber, and the bottom side of the scaffold is seeded. Then, the crossbar-bars construct with the scaffold may be inserted back into the bioreactor. The second groove may be slid cyclically to apply a cyclic load onto the scaffold again.

In another embodiment, the integrated bioreactor and reseeding chamber system may be used in a method of seeding cells onto a scaffold. The method may comprise securing a scaffold having a bottom side and a top side onto the first bar and the second bar of the bioreactor; sliding the second groove to stretch the scaffold; seeding the top side of the scaffold; flipping the crossbar-bars construct with the scaffold upside down in the bioreactor chamber; seeding the bottom side of the scaffold; and sliding the second groove to stretch the scaffold.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Hereinafter, the present invention will be described in more detail with reference to Examples. However, the scope of the present invention is not limited to the following examples.

EXAMPLES

Materials & Methods
Design and Construction of the Bioreactor/Reseeding Chamber System The bioreactor/reseeding chamber system was designed in 3-D computer aided design (CAD) modeling software SOLIDWORKS® (Waltham, MA) and AUTODESK® INVENTOR™ (San Rafael, CA). The subsequent fabrication of the various components was accomplished with either a MAKERBOT® REPLICATOR™ 2X 3-D printer using acrylonitrile butadiene styrene (ABS), or a BDSYSTEMS® ZPRINTER™ 450, with proprietary ZP150 powder and ZB63 binder. The rubber dividers were prototyped using FDA-compliant silicone rubber from MCMASTER-CARR® Robbinsville, NJ).

System Setup

Figure 8:
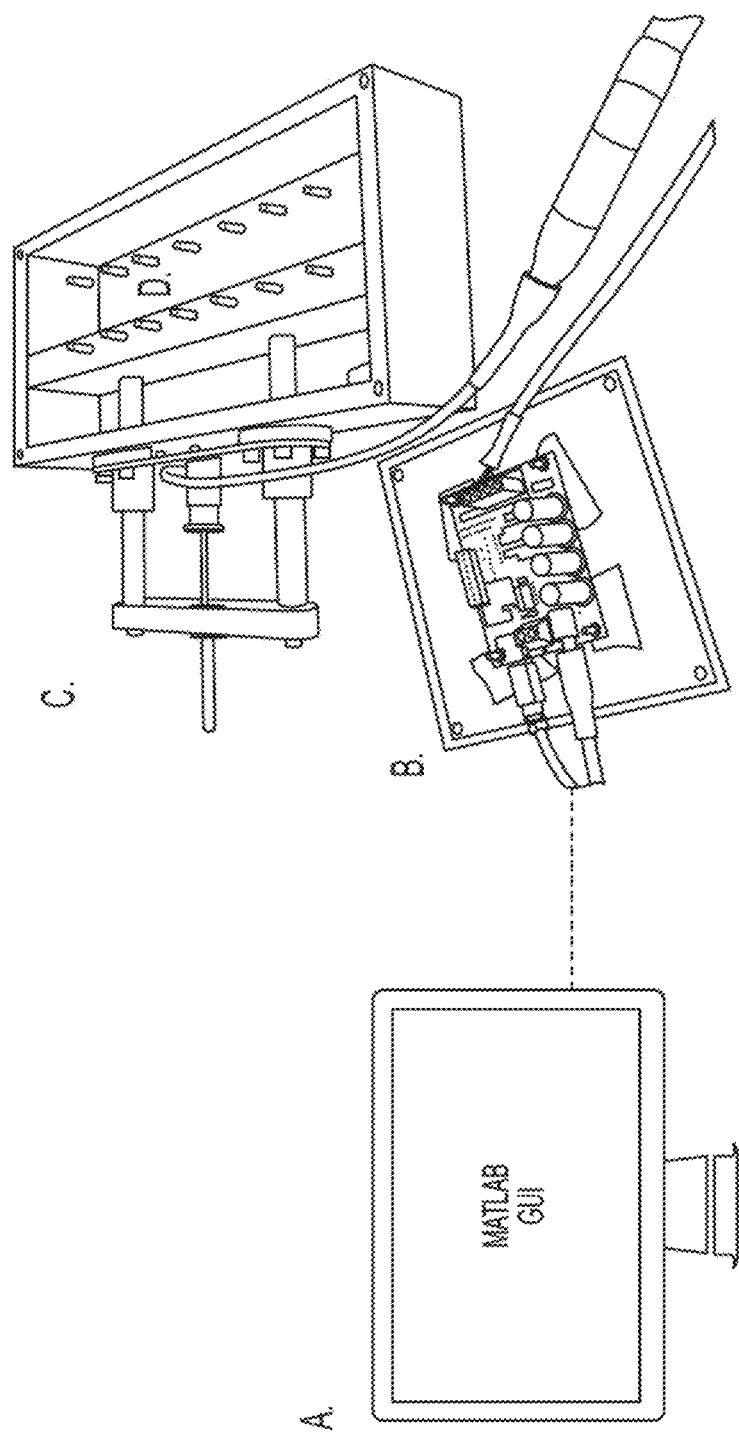
FIG. 8 shows a MATLAB GUI (A) controls the bipolar stepper (B) which is connected to a linear actuator (C) that moves a second groove in the bioreactor.
Figure 9:
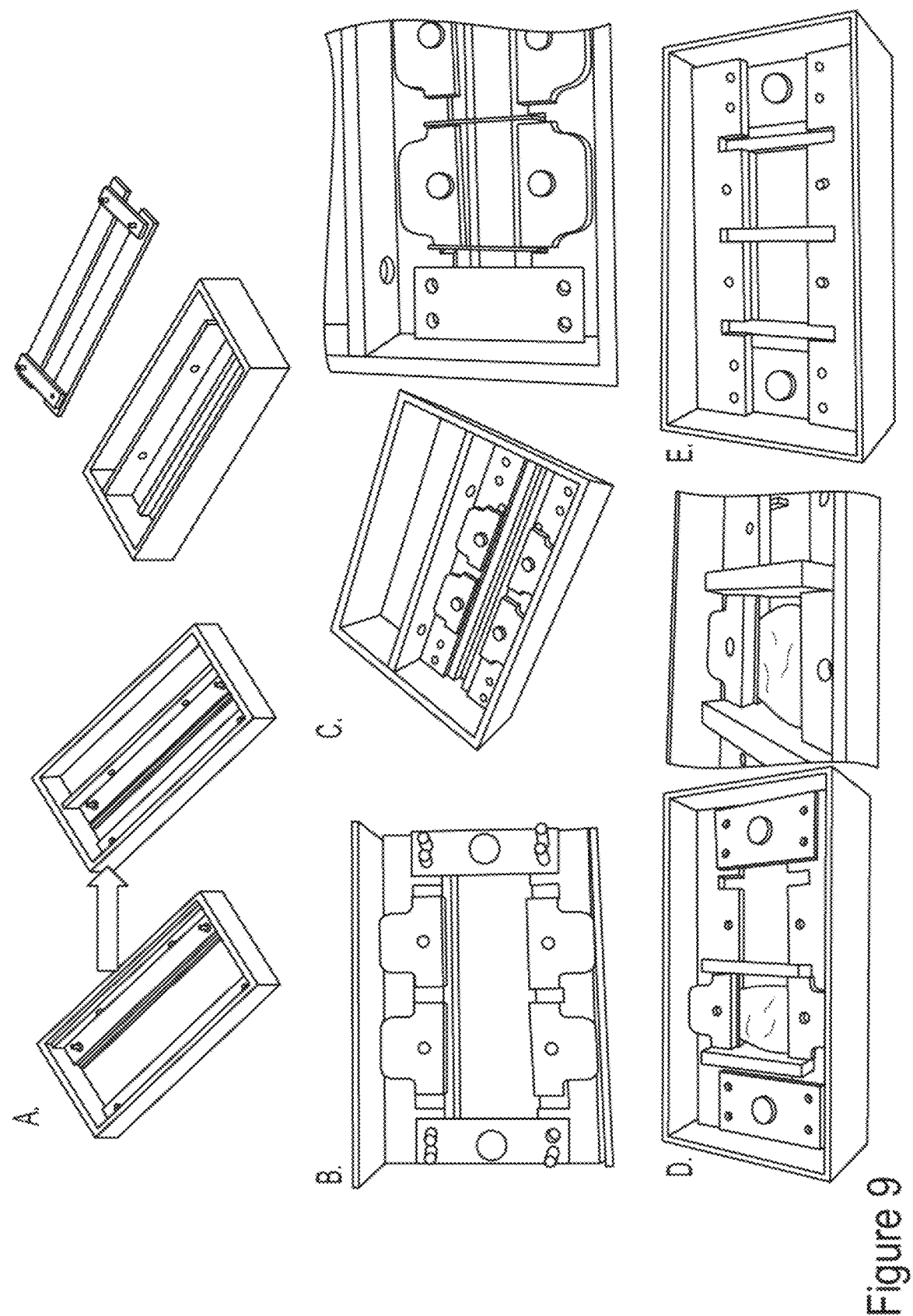
FIG. 9 shows design iterations of the bioreactor and reseeding chamber system. A) CAD drawing of the bioreactor system, illustrating how seeding and reseeding can all be done in the bioreactor. B) A prototype of another iteration of the crossbar-bars construct, which integrates with screws and tabs from the current system and features a knob added to the crossbar to improve usability. C) An ABS prototype that features a bioreactor/reseeding chamber system including a separate reseeding chamber design (right) and removable dividers. D) An ABS prototype that features rubberized dividers, and E) A Zprinter prototype that features fixed dividers in the reseeding chamber.

The present inventors connected a PHIDGET 1063 stepper motor (Calgary, Alberta) to a E43H4P-05-A01 linear actuator from HAYDON KERK (Waterbury, CT). The stepper motor is controlled by a MATLAB® graphical user interface (GUI) which allows the user to move a motor, wait, and repeat steps (FIG. 8).

GUI User Interface Testing

The GUI's usability was assessed by six biomedical engineers. Each test subject was taught how to use the old GUI and the new GUI, and allowed to practice using each GUI once. Then, they were asked to implement a five-step program for the bioreactor using the old and new GUIs, and the time it took them to write the program was recorded. Statistical significance was assessed using a one-tailed, paired t-test.

Results
Design Iterations

FIG. 9A illustrates the concept for the combined seeding and reseeding in the bioreactor itself. Grooves are attached to the motor. One groove is fixed in the bioreactor, and the other can slide in and out to apply cyclic stretch. The bar will be used to secure scaffolds, and they can be inserted into the grooves or removed for reseeding the other side of the scaffold. Crossbars can be screwed onto the bars perpendicularly to maintain the scaffold taut at a fixed distance, so that the bar/scaffold construct can be lifted out of the bioreactor for reseeding with minimal perturbation. The bar/scaffold construct is designed to be reinserted upside down back into the bioreactor to allow seeding of the underside of the scaffold. The present inventors' bioreactor system is designed to integrate with parts of the existing bioreactor, using the same tabs (in white) to securing scaffolds into the bioreactor (FIG. 9B). Crossbars are fixed by screws to the two scaffold bars, to keep them at a fixed position. Two knobs are added to the crossbars to allow for easier handling of the bar/scaffold construct.

However, a separate reseeding chamber is also designed to complement the bioreactor system (FIGS. 9B, D & E). The rationale behind a separate chamber for reseeding are to minimize the complexity to the bioreactor design, while simultaneously maximizing the flexibility for enhanced cell seeding in a smaller footprint (the novel reseeding chamber can lower the cost of good (i.e., reagents)). In order to maintain a compartment that holds in cell growth media over each scaffold during the cell attachment process, removable dividers are introduced into the design. These can be inserted into slots of the scaffold bar. In an attempt to improve the water tightness of each compartment, the present inventors' design featured rubberized dividers instead of plastic ones (FIG. 9D). The present inventors' "final" prototype (of a particular exemplary embodiment) may feature fixed dividers attached to the bottom of the bioreactor chamber (FIG. 9E).

However, a separate reseeding chamber is also designed to complement the bioreactor system (FIGS. 9B, D & E). The rationale behind a separate chamber for reseeding are to minimize the complexity to the bioreactor design, while simultaneously maximizing the flexibility for enhanced cell seeding in a smaller footprint (the novel re-seeding chamber can lower the cost of goods (i.e., reagents)). In order to maintain a compartment that holds in cell growth media over each scaffold during the cell attachment process, removable dividers are introduced into the design. These can be inserted into slots of the scaffold bar. In an attempt to improve the water tightness of each compartment, the present inventors' design featured rubberized dividers instead of plastic ones (FIG. 9D). The present inventors' "final" prototype (of a particular exemplary embodiment) may feature fixed dividers attached to the bottom of the bioreactor chamber (FIG. 9E).

Final Prototype

The reseeding chamber includes dividers that form compartments for each scaffold, in order to hold in cells and cell growth media during the cell seeding and reseeding process. The scaffold/bar construct can be inserted into the reseeding chamber both upside down and right side up, to allow multiple reseeding steps on either side of the scaffold.

Another embodiment of the present invention is an integrated bioreactor and reseeding chamber system, as shown in FIG. 7. The reseeding chamber is the same as the bioreactor chamber. The bioreactor chamber comprises dividers attached to a bottom of the bioreactor chamber. The dividers may form separate compartments inside the bioreactor chamber. The dividers may be plastic dividers. The combined bioreactor/reseeding chamber system would allow reseeding of cells on a scaffold in the same bioreactor chamber, thereby eliminating the process of moving the scaffold from a bioreactor chamber to another separate reseeding chamber.

Figure 10:
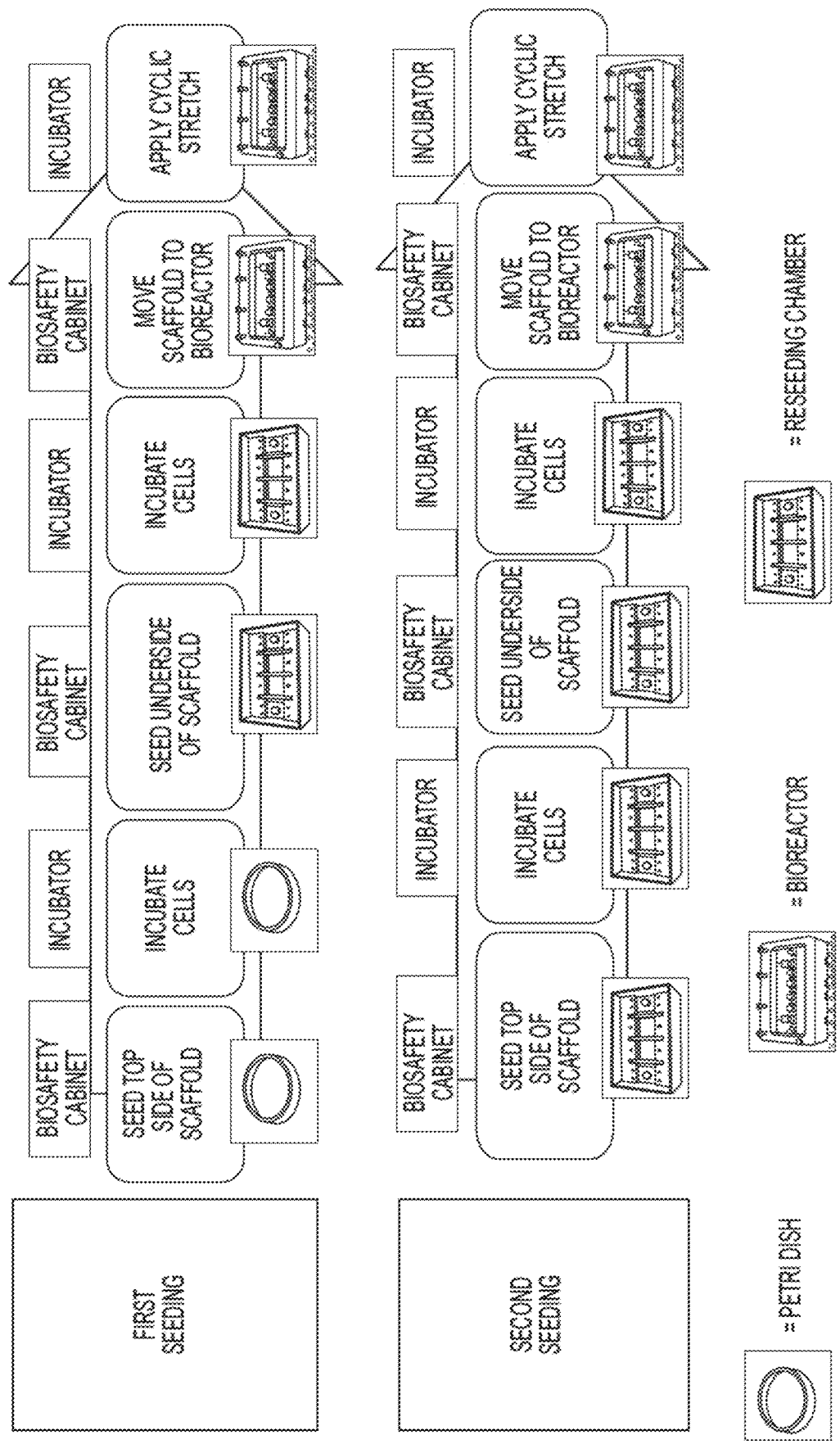
FIG. 10 shows a workflow using the new bioreactor/reseeding chamber system.

Using the present system, the initial seeding procedure is the same as the existing system and is done in a Petri dish. For subsequent seeding steps, the scaffold/bar construct can be removed from the bioreactor system, reseeded in the reseeding chamber, and then moved back to the bioreactor for application of cyclical mechanical stretch (FIG. 10).

GUI Testing

Figure 11:
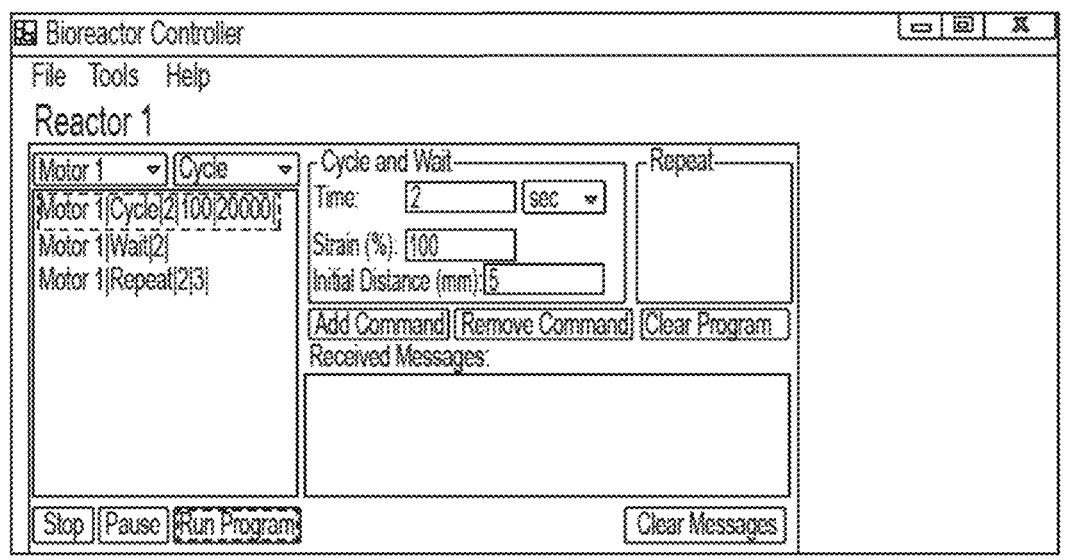
FIG. 11 shows user interfaces of A) the prior GUI and B) the new GUI.
Figure 11:
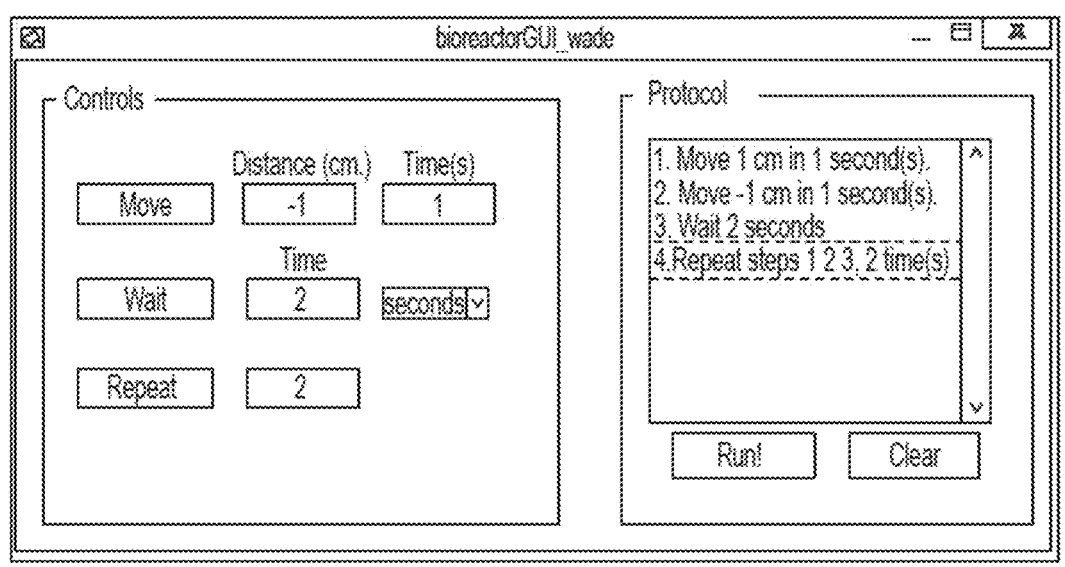
Figure 12:
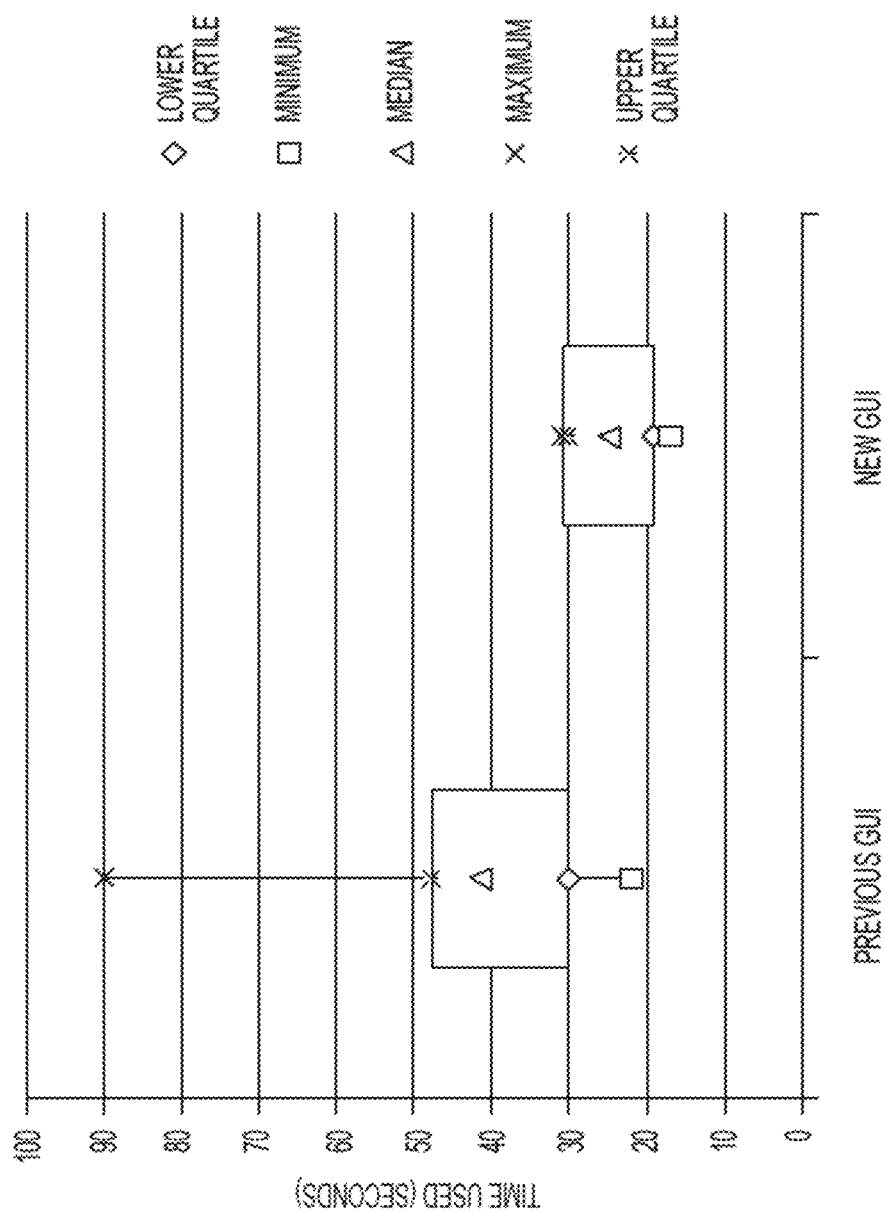
FIG. 12 shows the time used for six trained researchers (n=6) to program a cyclic stretch protocol using the prior GUI and the new GUI.

Using the new MATLAB® GUI (FIG. 11B), the number of steps, including mouse clicks and parameter inputs, for programming a standard cyclic stretch protocol was decreased from 29 steps using the previous GUI (FIG. 11A), to 18 steps using the new GUI. On average, the amount of time for trained researchers to write a simplified, 5-step program using the GUI decreased from 45 seconds for the old GUI, to 24 seconds for the new GUI, a 45% decrease in time (FIG. 12). The present inventors also received qualitative feedback from the users that the new GUI was much easier to learn, and easier to use. The new GUI is more user-friendly and allows for a faster work flow for programming the cyclic stretch protocol for the bioreactor system.

Here the present inventors provide, among other things, a modular bioreactor/reseeding chamber system that allows for multiple cell reseeding steps on the scaffold. The present inventors also implemented a MATLAB GUI for programming the protocol for applying cyclic stretch (FIG. 11). The GUI reduced the number of steps to program a typical work flow from 29 steps to 18 steps, and also allowed for a 46% decrease in the average time for a trained researcher to program a protocol (FIG. 12). The bioreactor/reseeding chamber system was modified throughout the design process to match the design criteria. A full-sized bioreactor and reseeding chamber system manufactured using Teflon enables biological testing using the entire system.

COMPARATIVE EXAMPLE—PRIOR BIOREACTOR

Figure 13:
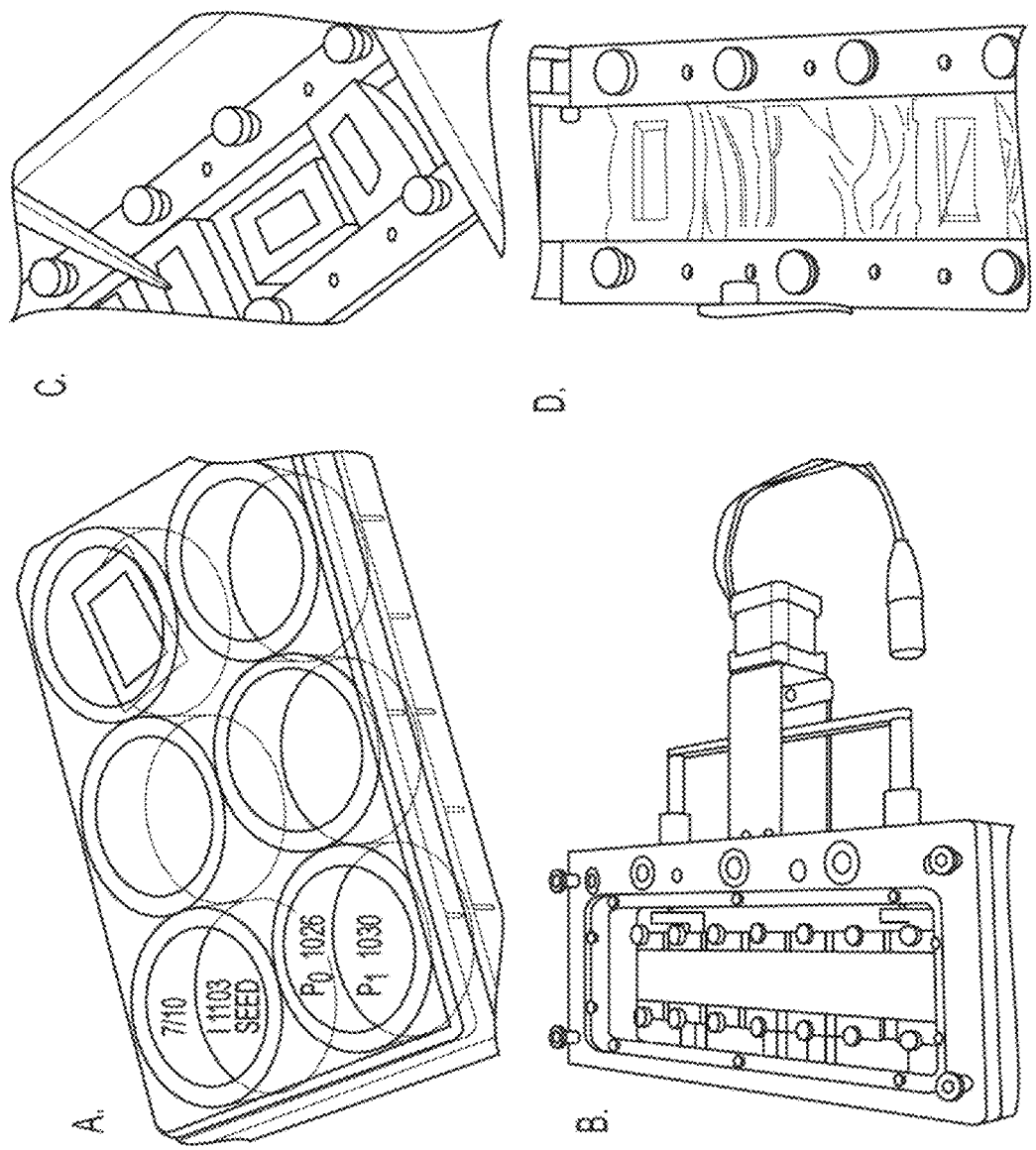
FIG. 13 shows A) Initial seeding of scaffolds using silicon molds. B) Scaffolds are conditioned for three days in the bioreactor. The prior bioreactor system can hold and condition up to eight scaffolds. C) The scaffolds are seeded a second time using silicon molds. D) Scaffolds then resume conditioning for another 2-3 days.

Using a prior bioreactor system, scaffolds are initially seeded with rat muscle precursor cells using a silicon mold and incubated under static conditions for ten days (FIG. 13A). The seeded scaffolds are then placed in the bioreactor for three days of bioreactor conditioning (FIG. 13B). Then, silicon molds are placed in the bioreactor, the myogenic media is removed from the bioreactor, and the top side of each scaffold is seeded a second time (FIG. 13C). After six hours of static incubation, myogenic media is restored to the bioreactor and the scaffolds resume conditioning for another 2-3 days (FIG. 13D).

What is claimed is:

1. A bioreactor, comprising:
a bioreactor chamber;
a first groove attached to the bioreactor chamber;
a second groove removably attached to the bioreactor chamber;
a first bar and a second bar,
wherein the second groove is capable of sliding back and forth along a direction perpendicular to the first groove;
the bioreactor further includes a crossbar-bars construct having at least one crossbar, and the at least one crossbar is attached to the first bar and the second bar to form the crossbar-bars construct;
the crossbar-bars construct with the crossbar attached to the first bar and the second bar is configured to be removably inserted into the bioreactor attached with the first groove and the second groove, in which the first bar and the second bar are removably inserted into the first groove and the second groove respectively; and
the crossbar-bars construct with the crossbar attached to the first bar and the second bar is configured to secure at least one scaffold onto the first bar and the second bar, and the crossbar-bars construct secured with the at least one scaffold is allowed to be lifted out of the bioreactor or inserted back into the bioreactor attached with the first groove and the second groove.

2. The bioreactor of claim 1, wherein the first groove is parallel to the second groove.

3. The bioreactor of claim 1, wherein the crossbar-bars construct is configured to allow the crossbar-bars construct to be lifted out of the bioreactor, to be turned upside down, and to be inserted back into the bioreactor attached with the first groove and the second groove.

4. The bioreactor of claim 3, wherein a knob is installed on the at least one crossbar.

5. A separate bioreactor and complementary reseeding chamber system, comprising
the bioreactor of claim 3; and
a reseeding chamber,
wherein the reseeding chamber is capable of housing the crossbar-bars construct.

6. The separate bioreactor and complementary reseeding chamber system of claim 5, wherein the reseeding chamber comprises dividers attached to a bottom of the reseeding chamber.

7. The separate bioreactor and complementary reseeding chamber system of claim 6, wherein the dividers are fixedly attached to the bottom of the reseeding chamber.

8. The separate bioreactor and complementary reseeding chamber system of claim 6, wherein the dividers are fixedly attached to the bottom of the reseeding chamber at even intervals.

9. The separate bioreactor and complementary reseeding chamber system of claim 6, wherein the dividers form separate compartments inside the reseeding chamber.

10. The separate bioreactor and complementary reseeding chamber system of claim 6, wherein the dividers are plastic dividers.

11. The separate bioreactor and complementary reseeding chamber system of claim 6, wherein there are three to eight dividers.

12. A method comprising seeding cells onto a scaffold employing the separate bioreactor and complementary reseeding chamber system of claim 6.

13. A method comprising seeding cells onto a scaffold employing the separate bioreactor and complementary reseeding chamber system of claim 5.

14. The method of seeding cells onto the scaffold of claim 13, comprising:
securing the scaffold having a bottom side and a top side onto the first bar and the second bar of the bioreactor;
sliding the second groove to stretch the scaffold;
moving the crossbar-bars construct with the scaffold from the bioreactor to the reseeding chamber;
seeding the top side of the scaffold;
turning the crossbar-bars construct with the scaffold upside down in the reseeding chamber;
seeding the bottom side of the scaffold;
moving back the crossbar-bars construct with the scaffold to the bioreactor; and
sliding the second groove to stretch the scaffold.

15. An integrated bioreactor and reseeding chamber system, comprising the bioreactor of claim 3, wherein the bioreactor chamber comprises dividers attached to a bottom of the bioreactor chamber.

16. The integrated bioreactor and reseeding chamber system of claim 15, wherein the dividers are fixedly attached to the bottom of the bioreactor chamber.

17. The integrated bioreactor and reseeding chamber system of claim 15, wherein the dividers form separate compartments inside the bioreactor chamber.

18. A method comprising seeding cells onto a scaffold employing the integrated bioreactor and reseeding chamber system of claim 15.

19. The method of seeding cells onto the scaffold of claim 18, comprising:
securing the scaffold having a bottom side and a top side onto the first bar and the second bar of the bioreactor;
sliding the second groove to stretch the scaffold;
seeding the top side of the scaffold;
flipping the crossbar-bars construct with the scaffold upside down in the bioreactor chamber;
seeding the bottom side of the scaffold;
sliding the second groove to stretch the scaffold.

20. The bioreactor of claim 1, wherein the first bar and the second bar are kept at fixed positions by the at least one crossbar for lifting the crossbar-bars construct out of the bioreactor or inserting the crossbar-bars construct into the bioreactor.

21. The bioreactor of claim 1, wherein the at least one crossbar is attached perpendicularly to the first bar and the second bar to form the crossbar-bars construct.

22. The bioreactor of claim 21, wherein the at least one crossbar is attached perpendicularly to a position at an end of the first bar and a position at an end of the second bar.

23. The bioreactor of claim 1, wherein the at least one crossbar is attached to the first bar and the second bar by screws.

24. The bioreactor of claim 1, further comprising two crossbars attached perpendicularly to both the first bar and the second bar to form the crossbar-bars construct, wherein the first bar and the second bar are kept at fixed positions by the two crossbars for lifting the crossbar-bars construct out of the bioreactor or inserting the crossbar-bars construct into the bioreactor.

25. The bioreactor of claim 24, wherein each of the two crossbars attaches perpendicularly to a position at an end of the first bar and a position at an end of the second bar.

26. The bioreactor of claim 24, wherein a knob is installed on each of the two crossbars, and the knob allows the crossbar-bars construct to be held to be lifted out of the bioreactor chamber or inserted back into the bioreactor chamber.

27. The bioreactor of claim 1, wherein each of the first bar and the second bar has at least one oval hole.

28. The bioreactor of claim 27, wherein each of the first bar and the second bar has two oval holes.

29. The bioreactor of claim 28, wherein each of the first bar and the second bar has the two oval holes positioned at both ends of the first bars and the second bars respectively.

30. The bioreactor of claim 1, wherein a scaffold securing member is installed on the first bar and the second bar respectively to form a pair facing each other.

31. The bioreactor of claim 1, wherein a number of scaffold securing members are installed on the first bar and the second bar respectively.

32. The bioreactor of claim 31, wherein each of the scaffold securing members include a tab.

33. The bioreactor of claim 1, wherein the bioreactor chamber is in a shape of a rectangular box.

34. The bioreactor of claim 1, wherein the second groove is connected to a motor, and the motor is capable of applying a cyclic load to the second groove, and the cyclic load is transferred from the second groove to the second bar.

35. The bioreactor of claim 1, further comprising a lid for the bioreactor chamber, wherein the lid contains holes for allowing air in and out of the bioreactor chamber.

36. A method comprising seeding cells onto a scaffold employing the bioreactor of claim 1.

* * * * *